United States Patent
Allmendinger et al.

(10) Patent No.: US 8,553,962 B2
(45) Date of Patent: Oct. 8, 2013

(54) TEMPORAL RESOLUTION IN CARDIO CT

(75) Inventors: Thomas Allmendinger, Forchheim (DE); Herbert Bruder, Höchstadt (DE); Thomas Flohr, Uehlfeld (DE); Rainer Raupach, Heroldsbach (DE); Harald Schöndube, Erlangen (DE); Karl Stierstorfer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 190 days.

(21) Appl. No.: 13/164,796

(22) Filed: Jun. 21, 2011

(65) Prior Publication Data

US 2011/0317901 A1    Dec. 29, 2011

(30) Foreign Application Priority Data

Jun. 23, 2010  (DE) .......................... 10 2010 024 684

(51) Int. Cl.
*G06K 9/00* (2006.01)
*A61B 6/00* (2006.01)

(52) U.S. Cl.
USPC .............................................. 382/131; 378/4

(58) Field of Classification Search
USPC ................. 382/128, 129, 130, 131, 132, 133, 382/134; 378/4, 8, 21–27, 101, 901; 600/407, 600/410, 411, 425, 427; 250/363.04; 424/904; 128/915, 916, 920, 922
See application file for complete search history.

(56) References Cited

U.S. PATENT DOCUMENTS

| | | | |
|---|---|---|---|
| 4,920,491 A * | 4/1990 | Eberhard et al. | 382/131 |
| 6,442,288 B1 * | 8/2002 | Haerer et al. | 382/128 |
| 6,728,331 B1 * | 4/2004 | McDaniel et al. | 378/4 |
| 7,020,234 B2 * | 3/2006 | Bruder et al. | 378/8 |
| 8,345,817 B2 * | 1/2013 | Fuchs et al. | 378/10 |
| 2010/0303326 A1 | 12/2010 | Allmendinger | |
| 2011/0033097 A1 | 2/2011 | Bruder et al. | |

FOREIGN PATENT DOCUMENTS

| | | |
|---|---|---|
| DE | 102007029731 A1 | 1/2009 |
| DE | 102007029731 A1 | 1/2009 |
| DE | 102009022679 A1 | 12/2010 |
| DE | 102009022679 A1 | 12/2010 |
| DE | 102009036232 A1 | 2/2011 |

OTHER PUBLICATIONS

German Patent Publication DE10 2010 024 684.0, filed on Jun. 23, 2010 (not yet published).

* cited by examiner

*Primary Examiner* — Abolfazl Tabatabai
(74) *Attorney, Agent, or Firm* — Harness, Dickey & Pierce, P.L.C.

(57) ABSTRACT

A method is disclosed for the reconstruction of picture data of a moving object under examination from measurement, with the measurement data having been recorded beforehand for a relative rotational movement between a radiation source of a computed tomography system and the object under examination. In at least one embodiment, first picture data is computed from a complete measurement dataset of the measurement data for a picture reconstruction, and second picture data is computed from an incomplete measurement dataset for a computed tomography picture reconstruction. The first picture data and the second picture data are combined into third picture data, with the combination being computed using location-dependent movement information of the object under examination.

24 Claims, 5 Drawing Sheets

TEMPORAL RESOLUTION IN CARDIO CT

PRIORITY STATEMENT

The present application hereby claims priority under 35 U.S.C. §119 on German patent application number DE 10 2010 024 684.0 filed Jun. 23, 2010, the entire contents of which are hereby incorporated herein by reference.

FIELD

At least one embodiment of the invention generally relates to a method for the reconstruction of picture data of an object under examination from measurement data, with the measurement data having been recorded during a relative rotational movement between a radiation source of a computed tomography system and the object under examination.

BACKGROUND

Tomographic imaging methods are characterized by enabling the internal structures of an object under examination to be examined without having to carry out operational interventions on said structures. One possible type of tomographic imaging includes recording a number of projections from different angles. A two-dimensional slice picture or a three-dimensional volume picture of the object under examination can be computed from these projections.

Computed tomography is an example of this type of tomographic imaging method. Methods for scanning an object under examination with a CT system are generally known. Typical methods employed in such cases are orbital scans, sequential orbital scans with advance or spiral scans. Other types of scans which are not based on circular movements are also possible, such as scans with linear segments for example. Absorption data of the object under examination is recorded from different recording angles with the aid of at least one X-ray source and at least one detector lying opposite said source and this absorption data or projections collected in this way are computed by means of appropriate reconstruction methods into picture slices through the object under examination.

For the reconstruction of computed-tomographic pictures from X-ray CT datasets of a computed-tomography device (CT device), i.e. from the recorded projections, what is known as a Filtered Back Projection (FBP) is used nowadays as the standard method. After the data has been recorded, a so-called "rebinning" step is executed in which the data generated with the beam spreading out in the form of a fan is rearranged such that it is available in a form such as would occur had the detector been hit by X-rays arriving at the detector in parallel. The data is then transformed into the frequency range. A filtering is undertaken in the frequency range and subsequently the filtered data is back transformed. With the aid of the data sorted out and filtered in this way, a back projection is then carried out onto the individual voxels within the volume of interest.

A disadvantage of this generally-known computation method lies in the fact that with a moving object under examination or an object under examination which moves at least in part, movement imprecision can arise in the picture, since during the period of a scanning process for the data which is needed for a picture a local displacement of the object under examination or of a part of the object under examination can occur, so that the basic data which leads to the picture does not all reflect spatially identical situations of the object under examination. This movement imprecision problem arises particularly acutely during the execution of cardio CT examinations of a patient for whom, as a result of the heart movement, a strong movement imprecision can occur in the area of the heart or for examinations in which relatively rapid changes in the object under examination are to be measured.

The undesired movement artifacts are reduced by the temporal resolution of the CT imaging being increased. There are various methods of doing this. On the one hand it is possible to shorten the rotation time of the gantry. However in this case, mechanical restrictions are soon encountered since the centrifugal force exerted on the components increases quadratically as the rotation time reduces.

On the other hand, as part of the picture reconstruction, by using phase-equivalent angle-complementary data of adjacent heart cycles, the temporal resolution can be improved. However the benefit depends on the ratio of the heart rate to the gantry circulation time and is barely able to be influenced.

Finally two-emitter CT systems have been developed, i.e. CT devices with two X-ray sources and detectors assigned to them. In accordance with the halved measurement time as a result of the presence of two X-ray source-detector systems, these make a doubled temporal resolution possible. The disadvantage in this case is that the costs for the duplicated design of the core components, such as emitter, detector etc., are significant.

SUMMARY

At least one embodiment of the invention demonstrates a method for the reconstruction of CT pictures in which account is to be taken of the fact that movements of the object under examination can be present. A corresponding control and processing unit, a CT system, a computer program and a computer program product are also to be demonstrated.

At least one embodiment of the invention is directed to method, a control and processing system, a CT system, a computer program and a computer program product. Advantageous embodiments and developments are the subject matter of subclaims.

In at least one embodiment of the inventive method for the reconstruction of picture data of a moving object under examination from measurement data, this data has previously been recorded in a relative rotational movement between a radiation source of a computed tomography system and the object under examination. First picture data is computed from a complete measurement dataset of the measurement data for a computed tomography picture reconstruction, and second picture data is computed from an incomplete measurement dataset of the measurement data for a computed tomography picture reconstruction. The first picture data and the second picture data are combined into third picture data, with the combination being computed using location-dependent movement information of the object under examination.

On the one hand a complete set of measurement data from the recorded measurement data is used in order to reconstruct the first picture data from said dataset. This reconstruction can be undertaken in a manner known per se, e.g. by FBP. The completeness of the measurement dataset means for a measurement in cone beam geometry that projections over a contiguous projection angle range of 180° plus the cone beam opening angle will be used for picture reconstruction. After the parallel re-binning, i.e. the rearrangement of the measurement data into parallel beam geometry, the minimum length of the reconstruction interval thus amounts to 180°.

An incomplete measurement dataset of the measurement data is also used in order to reconstruct the second picture data from this dataset. This incomplete measurement dataset thus includes projections over a contiguous projection angle range, which is smaller than the values of 180° or 180° plus the cone beam opening angle specified above.

As a result of the incompleteness of the measurement dataset used the second picture data has artifacts. Of advantage with the second picture data is however that during the recording of the measurement dataset less time elapses than for the first picture data, so that movement artifacts are less pronounced. The latter is the reason why the second picture data is used.

The first and the second picture data map the same slice of the object under examination. In this way it is possible, through a combination of the first and the second picture data, to obtain the third picture data which can be output as result picture data. The first and also the second picture data can involve two-dimensional sectional slices or three-dimensional volume representations of the object under examination or parts of the object under examination.

In the combination of the first with the second picture data, the movement of the object under examination during the measurement data recording is taken into account. The movement information used for this purpose is location-dependent. This means for example that a value constantly showing the movement is not simply used for the entire picture data. Instead the movement information changes dependent on the location within the object under examination; this can mean a change in the movement information from pixel to pixel of the picture data.

In a development of at least one embodiment of the invention, the second picture data is computed by frequency components of the first picture data being removed. This means that the second picture data is not computed independently of the first picture data, but rather the second picture data is determined from the first picture data after computation of the first picture data. For this purpose, a Fourier transformation of the first picture data is undertaken beforehand. The picture data can be presented both in the location space and also in the frequency space, with a switch able to be made between the two spaces through a multidimensional Fourier transformation.

With two-dimensional slice pictures a two-dimensional Fourier transformation has to take place to do this, with three-dimensional volume pictures a three dimensional Fourier transformation. In the frequency representation of the first image data parts of the image data are then removed in order to arrive at the second picture data.

Advantageously the removal of the frequency components is undertaken by applying a filter function. This filter function can be applied in the frequency space to the frequency space representation of the first picture data. In this case the filter function preferably corresponds to a cutting out of two conical components and a partial refilling of these cone-shaped components. This can be imagined as a mask with the described pattern of the partly filled out cone which is laid over the frequency space representation of the first picture data. It is especially advantageous if during the removal an area of small frequencies exists in which no picture data is removed and an area of larger frequencies in which picture data is removed. In this way the second picture data does not lack any small frequency information in which the contrast information of the pictures is contained compared to the first picture data. The area of small frequencies is preferably circular. On the other hand larger frequency information is missing which contains the movement artifacts of the first picture data.

In accordance with another development, the second picture data is computed by components of the complete measurement dataset being removed and the second picture data being computed from this. This involves an alternate procedure for removing the picture data in the frequency representation. By removal in the measurement data space the complete measurement dataset of the first picture data becomes the incomplete measurement dataset of the second picture data. The measurement data removal is preferably undertaken so that, after a computation of the second picture data based on this incomplete measurement data, the pattern explained above in the frequency representation of the second picture data exists.

Preferably the incomplete measurement dataset is a subset of the complete measurement dataset. This means that the first and the second picture data map the object under examination at the same point in time, whereby the temporal resolution of the first picture data is smaller than that of the second picture data.

In an embodiment of the invention, the incomplete measurement dataset lies centrally within the complete measurement dataset. This central arrangement means that the central of the projection angles of the two datasets is the same. As a result of its incompleteness the incomplete measurement dataset is smaller than the complete dataset, so that it is arranged completely within the complete measurement dataset.

In a development of the invention, the combination is computed as a pixel-by pixel weighted sum of the first and the second picture data. In this case preferably at least one weighting factor is used which contains the movement information. This weighting factor can be used for weighting the first and/or the second picture data. It is especially advantageous for the weighting factor to contain location-dependent noise information of the first picture data. This noise information can be used for example in the form of a contrast-to-noise ratio of the movement of the object under examination, i.e. a ratio between the picture changes through movement and the picture noise. The contrast-to-noise ratio can be a component of an exponential function for example.

It is especially advantageous, in the combination in moving picture regions, for the second picture data to preferably contribute to the third picture data and in static picture regions for the first picture data to preferably contribute to the third picture data. This makes it possible in moving picture regions to avoid movement artifacts without having to accept a picture deterioration compared to the first picture data in moving picture regions.

In an embodiment of the invention, the location-dependent movement information is obtained by fourth picture data being computed and compared pixel-by-pixel with the first picture data. The fourth picture data in this case is preferably offset slightly in time in relation to the first picture data, so that it can be established by a comparison in a location-dependent manner how greatly the object under examination has moved at the point of mapping by the first picture data or the recording of the complete measurement dataset of the first picture data.

In an embodiment of the invention, a timespan of the object under examination with lower movement is determined, with the complete measurement dataset having been recorded during this timespan. In this way a measurement dataset is selected from the recorded measurement data which is favorable in respect of the movement phase, so that this measurement dataset is included for the first picture data.

In a development of an embodiment of the invention, a plurality of second picture data and, through combination with the first picture data, a plurality of third picture data is computed, and result picture data is selected from the plurality of the third picture data. The method described above is thus executed multiple times so that the plurality of the third picture data is present. This makes it possible to output the best or best possible picture data as a result.

It is especially advantageous for the plurality of second picture data to differ from one another through the position of the respective incomplete measurement dataset within the complete measurement dataset. In this case a first position of the incomplete measurement dataset within the complete measurement dataset can thus be defined, from which first and second picture data results, after which subsequently a second position of the incomplete measurement dataset within the complete measurement dataset is defined, from which second picture data results, etc.

The result picture data is selected by applying a picture standard to the plurality of the third picture data. This picture standard can be adapted to criteria which represent a measure for the picture quality.

At least one embodiment of the inventive control and processing unit is used for the reconstruction of picture data of an object under examination from measurement data of a CT system. In at least one embodiment, it comprises a program memory for storing program code—with program code being present therein—if necessary among other data, which is suitable for executing at least one embodiment of a method of the type described above or for bringing about or controlling this execution. At least one embodiment of the inventive CT system includes such a control and processing unit. It can also contain other components, which are needed for example for recording measurement data.

At least one embodiment of the inventive computer program has program code which is suitable for executing the method of the type described above when the computer program is executed on a computer.

At least one embodiment of the inventive computer program product comprises program code segments stored on a computer-readable data medium which are suitable for carrying out at least one embodiment of the method of the type described above when the computer program is executed on a computer.

BRIEF DESCRIPTION OF THE DRAWINGS

The invention will be explained in greater detail below on the basis of an example embodiment. The figures show.

DETAILED DESCRIPTION OF THE EXAMPLE EMBODIMENTS

Figure 1:
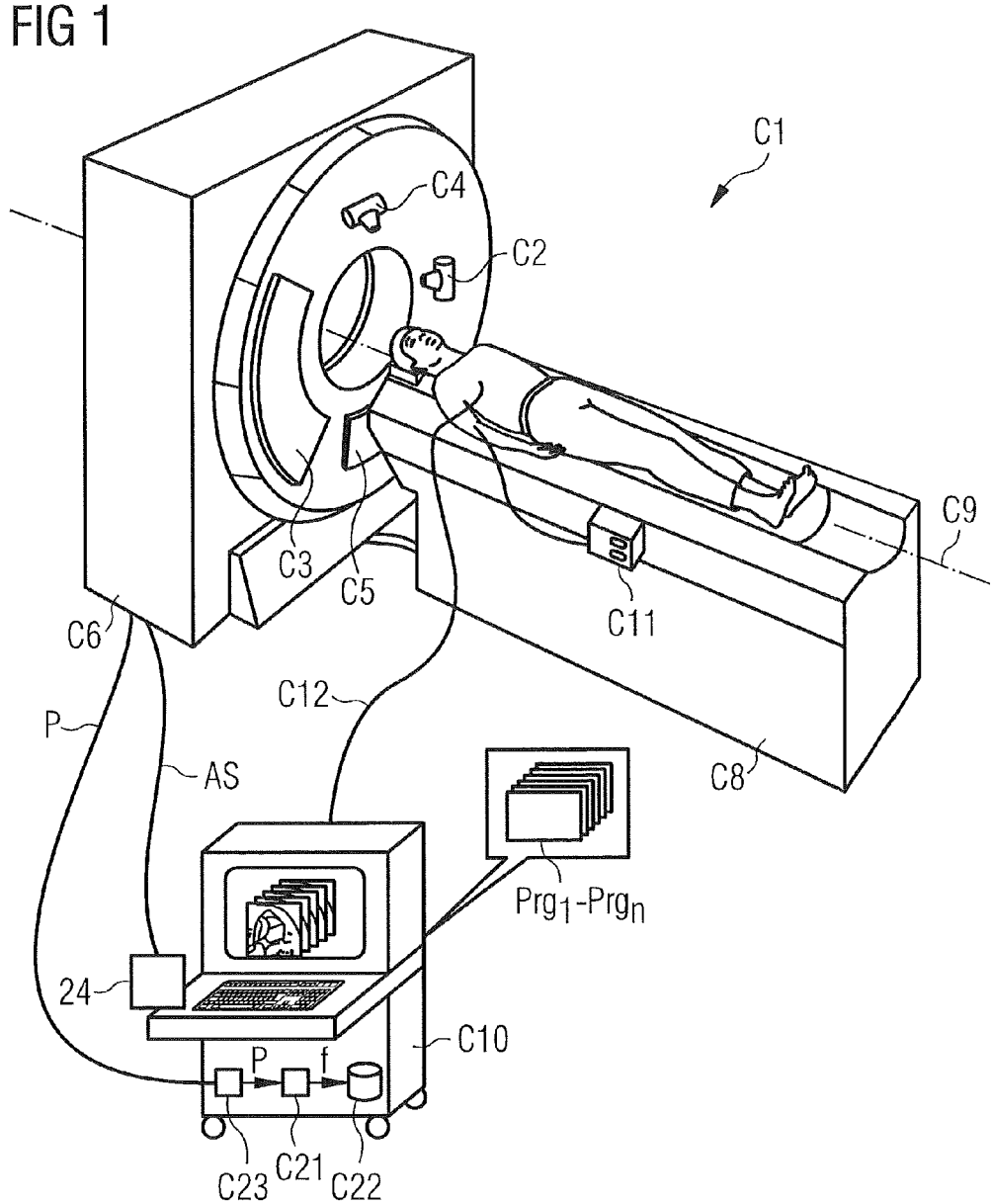
FIG. 1: a first schematic diagram of an example embodiment of a computed tomography system with a picture reconstruction component.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 first shows a schematic diagram of a first computed-tomography system C1 with a picture reconstruction device C21. This involves what is known as a third-generation CT device, to which the invention is not restricted however. Located in the gantry housing C6 is a closed gantry not shown in the diagram on which are arranged a first X-ray tube C2 with a detector C3 lying opposite it. Optionally arranged in the CT system shown here are a second X-ray tube C4 with a detector C5 lying opposite it, so that a higher temporal resolution can be achieved by the radiator/detector combination additionally available, or with the use of different X-ray energy spectra in the radiator/detector system, dual-energy examinations can be undertaken.

The CT system C1 also comprises a patient couch C8 on which the patient can be pushed during the examination along a system axis C9, also referred to as the z-axis, into the measurement field, with the scanning itself able to occur both as a pure orbital scan without forward movement of the patient exclusively in the region of interest under examination. The movement of the patient couch C8 relative to the gantry is effected by a suitable motorization. In this case the X-ray source C2 or C4 respectively rotates around the patient. In such cases the detector C3 or C5 respectively moves in parallel in relation to the X-ray source C2 or C4 in order to record projection measurement data, which is then used for the reconstruction of picture slices.

As an alternative to a sequential scan in which the patient is pushed step-by step between the individual scans through the examination field, there is naturally also the option provided of a spiral scan, in which the patient is pushed continuously during the orbital scanning with the X-rays along the system axis C9 through the examination field between X-ray tube C2 or C4 respectively and detector C3 or C5 respectively. The movement of the patient along the axis C9 and the simultaneous orbital movement of the X-ray source C2 or C4 respectively produces a helical track for a spiral scan for the X-ray source C2 or C4 relative to the patient during the measurement. This track can also be achieved by the gantry being moved along the axis C9 while the patient does not move. It is also possible to move the patient continuously and periodically backwards and forwards between two points.

The CT system 10 is controlled by a control and processing unit C10 with a computer program code $Prg_1$ through $Prg_n$ present in a memory. It should be noted that these computer program codes $Prg_1$ to $Prg_n$ can naturally also be contained on an external storage medium and loaded in the control and processing unit C10 as required.

From the control and processing unit C10 acquisition control signals AS can be transmitted via a control interface 24 in order to control the CT system C1 in accordance with specific measurement protocols. The acquisition control signals AS relate in such cases for example to the X-ray tubes C2 and C4, with specifications able to be given about their power and the times at which they are switched on and switched off, as well as the gantry, with specifications able to be provided about its speed of rotation as well as the advance of the couch.

Since the control and processing unit C10 has an input console, measurement parameters can be entered by a user or operator of the CT device C1 which then control the data recording in the form of acquisition control signals AS. Information about measured parameters currently used can be shown on the screen of the control and processing unit C10; in addition further information relevant for the operator can be displayed.

The projection measurement data p or raw data acquired by detector C3 or C5 is transferred via a raw data interface C23 to the control and processing unit C10. This raw data p is then, if necessary after suitable pre-processing, further processed in a picture reconstruction component C21. The picture reconstruction component C21 is realized in this example embodiment in the control and processing unit C10 in the form of software on a processor, e.g. in the form of one or more of the computer program codes $Prg_1$ through $Prg_n$. What has already been stated in relation to image reconstruction applies in relation to the control of the measurement process, that the computer program codes $Prg_1$ to $Prg_n$ can also be contained on an external storage medium and can be loaded if necessary into the control and processing unit C10. It is also possible for the control of the measurement process and the picture reconstruction to be carried out by different processing units.

The picture data f reconstructed by the picture reconstruction component C21 is then stored in a memory C22 of the control and processing unit C10 and/or output in the usual way on the screen of the control and processing unit C10. It can also be fed via an interface not shown in FIG. 1 into a network connected to the computed-tomography system C1, for example a radiological information system (RIS) and stored in mass storage accessible in this system or output as pictures.

The control and processing unit C10 can additionally also execute the function of an EKG, with a line C12 being used for deriving the EKG potentials between patient and control and processing unit C10. In addition the CT system C1 shown in FIG. 1 also has a contrast media injector C11 via which additional contrast media is injected into the blood circulation of the patient so that the blood vessels of the patient, especially the heart chambers of the beating heart, can be better represented. In addition there is also the opportunity of carrying out perfusion measurements for which the suggested method is likewise suitable.

Figure 2:
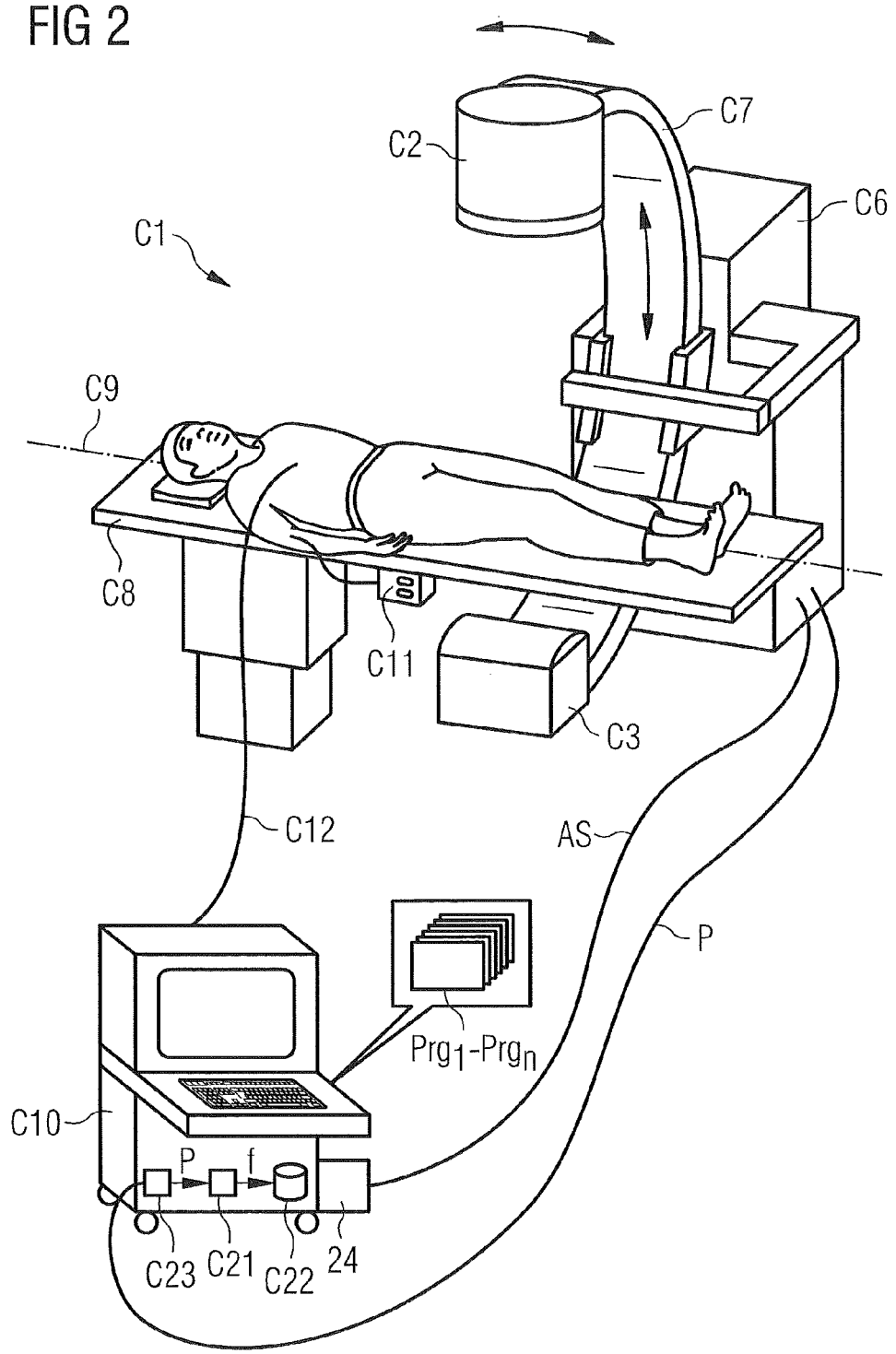
FIG. 2: a second schematic diagram of an example embodiment of a computed tomography system with a picture reconstruction component.

FIG. 2 shows a C-arm system, in which, by contrast with the CT system of FIG. 1, the housing C6 carries the C-arm C7, to one side of which is attached the X-ray tube C2 and to the opposite side the detector C3. The C-arm C7 is likewise hinged around a system axis C9 for a scan, so that a scan can be undertaken from a plurality of scanning angles and corresponding projection data p can be determined from a plurality of projection angles. The C-arm system C1 of FIG. 2, like the CT system from FIG. 1, has a control and processing unit C10 of the type described for FIG. 1.

An embodiment of the invention is able to be used in both of the systems shown in FIGS. 1 and 2. Furthermore it is basically also able to be used for other CT systems, e.g. for CT systems with a detector forming a complete ring.

Where pictures are to be recorded of parts of a patient's body which do not move or can be kept still, there are no significant problems with movement artifacts for recording the projections and for the subsequent picture reconstruction. By contrast, this situation is critical for moving objects under examination. The situation is considered below in which a CT picture of a moving object under examination is to be recorded.

An example of an object under examination which moves periodically is the human heart. An embodiment of the invention will be explained below in greater detail with reference to cardio CT, i.e. a CT picture of the beating heart. Naturally, this application is not restricted to this example embodiment.

Figure 3:
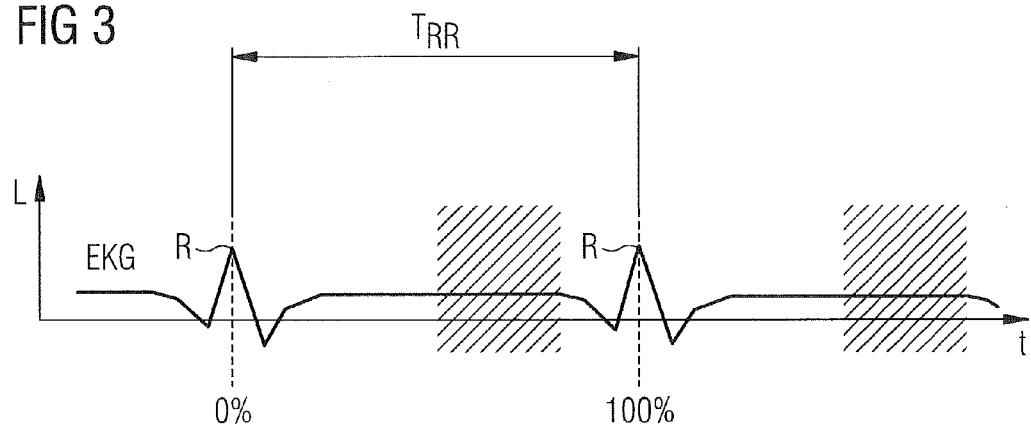
FIG. 3: the movement cycle of the human heart.

It is well known that the human heart carries out a periodic movement. The periodic movement consists in this case of an alternating sequence or a rest or sleep phase and a movement or beating phase. The rest phase has a duration of usually between 500 to 800 ms, the beating phase has a duration of between 200 and 250 ms. This can be seen from FIG. 3, in which the level L of the EKG signal labeled EKG of a patient is plotted over the time t. The EKG signal illustrates the periodic movement of the heart of the patient, with the beginning of a heart cycle being determined by R wave R and the duration of the respective heart cycle by the RR interval $T_{RR}$, i.e. by the distance between the R wave R initiating the heart cycle and the R wave R initiating the following heart cycle. A heart phase starts with an R wave R at 0% and ends at the next R wave R at 100%. The conversion between the dimension of the time and the heart phase is possible at any time; EKG data can be used for this purpose, which indicates at any given point in time which heart phase is actually present. The rest phase of the heart, i.e. the phase of minimal heart movement, is indicated by dashed lines in each case.

In heart imaging, by way of CT the heart phase during which the data is recorded is decisive for a good picture quality. An attempt is thus usually made to use data for the picture reconstruction which was recorded during a heart phase with little or minimal heart movement.

As well as the existing requirements relating to the quality of CT pictures for objects under examination which do not move, there is the objective with heart recordings of achieving a high temporal resolution of the pictures. The temporal resolution in this case is inversely proportional to the period of time which is needed for detecting the projections. The more time elapses during the data recording the more the heart moves during this measurement time. This movement leads to undesired movement artifacts in the CT pictures. The expressiveness of the CT is drastically reduced by this. For mid-range CT devices the rotation time per gantry orbit amounts to approx. 450-500 ms.

For CT picture reconstructions with measurements in parallel beam geometry a data interval, i.e. a series of consecutive projections, with each projection corresponding to a measurement at a specific angle of projection, must be available which corresponds to at least one half orbit of the X-ray source around the object under examination, i.e. a projection angle range of 180°. With a cone beam geometry the projection angle range must amount to 180° plus the cone opening angle. Both cases are grouped together below under the designation "data of a half orbit" or "complete dataset". This minimum data interval is necessary to be able to reconstruct each pixel in the measurement field. In the center of rotation a projection angle range of 180° is also sufficient in cone beam geometry. The best possible temporal resolution in a CT picture reconstructed in this way thus amounts in the vicinity of the center of rotation to precisely half the rotation time of the CT device.

Figure 4:
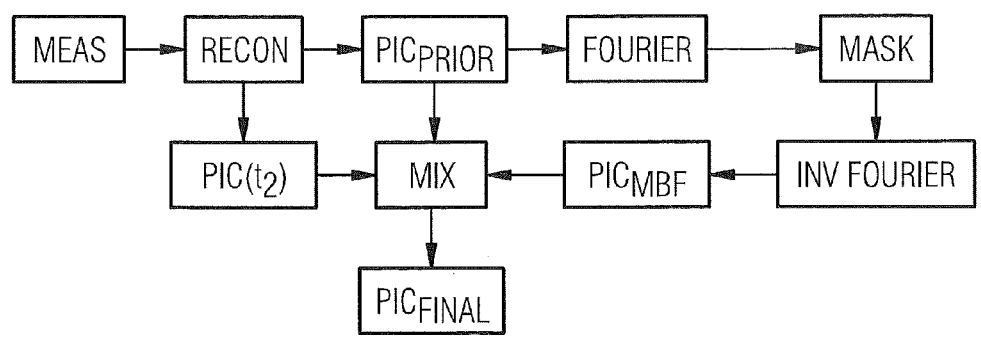
FIG. 4: a flow diagram.

The way in which the temporal resolution for cardio CT pictures can be improved by a picture-based method is presented below with reference to the flow diagram shown in FIG. 4. The picture-based method has the advantage of no interventions into the hardware of the CT device being necessary, which are generally expensive and approach the limits of what is technically possible. The significant factor in the method explained below is the use of a suitable picture filter.

First of all in the step MEAS the measurement data is recorded. In this case the number of complete measurement datasets are recorded for each slice of the object under examination to be mapped, so that for each slice to be mapped pictures of different movement states can be reconstructed, i.e. in a cardio CT as pictures of different heart phases.

After the measurement data recording MEAS, in step REKON, a CT picture $PIC_{PRIOR}$ is reconstructed from the data of a half orbit. A conventional reconstruction methods such as FBP for example is used to do this. The pictures are reconstructed for each slice of the region of interest of the object under examination i.e. usually for each slice of the heart. Thus a stack of pictures is available which includes a series of two-dimensional slice pictures $PIC_{PRIOR}$.

The picture $PIC_{PRIOR}$ corresponds to the optimum or at least a best possible heart phase. The optimum or a good heart phase respectively is characterized by little movement being present. This can be achieved by pictures of different heart phases being reconstructed and for each slice the picture being sought which has the fewest possible movement artifacts. As an alternative to this more complex procedures are also conceivable, i.e. the use of a motion map. Motion mapping methods compute correlations between temporally-adjacent pictures; such methods are described for example in document DE 102007029731 A1, as well as in the subsequently published application DE 10 2009 022 679.6, the entire contents of each of which are hereby incorporated herein by reference.

Figure 5A:
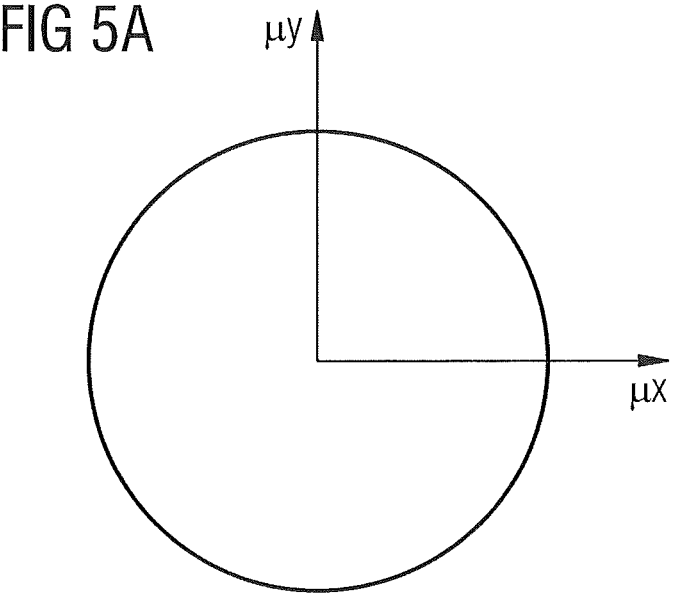
FIG. 5: the presence of picture data in the frequency space

Each of these pictures $PIC_{PRIOR}$ is subjected to a two-dimensional Fourier transformation FOURIER. This Fourier transformation FOURIER effects a switch from the location space into the frequency space of the picture. The presence of picture data in the frequency space is illustrated in the frequency space diagram of FIG. 5A. Plotted on the axes are the two frequencies $\mu x$ and $\mu y$. As also in FIGS. 5B and 6 below, this involves a representation in polar coordinates. The frequencies for which picture data is present can be taken from the representation. It can be seen that in the picture $PIC_{PRIOR}$ picture data is present for all frequencies up to a maximum frequency. The reason for the presence of picture data of all frequencies lies in the fact that picture $PIC_{PRIOR}$ is based on a complete dataset.

Figure 5B:
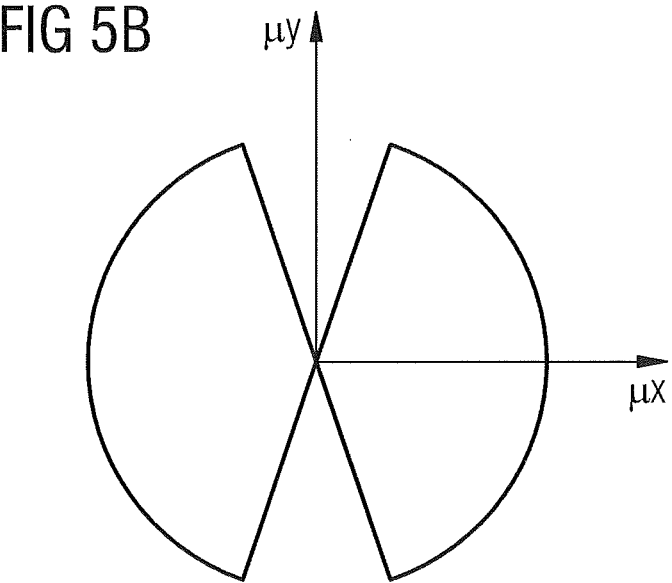

If an incomplete dataset is used for the reconstruction of a CT picture, the frequency space representation depicted in FIG. 5B would be produced. Because of the incomplete angular sampling each missing projection in accordance with the Fourier slice theorem brings missing picture data in the corresponding direction in the Fourier spectrum of the picture with it. This missing picture data corresponds to cones which are cut out of the complete dataset. In particular picture data is missing for frequencies amounting to a large number.

Figure 6:
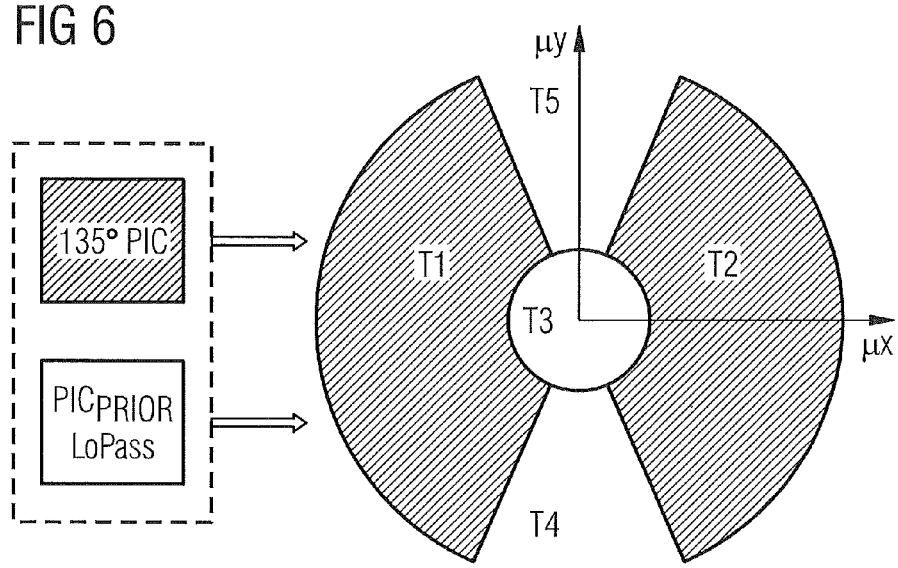
FIG. 6: a masking of picture data in the frequency space.

In the next step MASK the picture data in the frequency space is masked, which is explained on the basis of FIG. 6. The masking corresponds to a specific frequency filtering; i.e. picture data is removed in the frequency space by the masking. As shown with reference to FIG. 5A, picture data is originally present for all frequencies in the picture $PIC_{PRIOR}$. This is reduced by the components T4 and T5 shown in white in FIG. 6, i.e. the picture data is removed from the frequency areas T4 and T5. Thus the components T1, T2 and T3 of the picture data are left over in the frequency space after the masking.

The part T1 and T2 of the masked picture data shown dark corresponds to the diagram depicted in FIG. 5B. (By contrast with FIG. 5B the picture data of the small frequencies are covered by the bright circle of area T3, which will be explained in greater detail below). I.e. this part T1 and T2 of the picture data would be obtained if a CT picture were to be reconstructed from an incomplete measurement dataset. Accordingly it is specified on the left-hand side of FIG. 6 that this part T1 and T2 of the picture data corresponds to a picture 135° PIC reconstructed from a 135° measurement interval, referred to below as the tomosynthesis picture. Naturally, instead of a 135° section, another angular area which is smaller than a half orbit can be used, e.g. an area of 120°. This tomosynthesis picture thus corresponds in the measurement data area to a section of the complete 180° sinogram.

The tomosynthesis picture has the advantage over the picture $PIC_{PRIOR}$ of containing fewer movement artifacts. This is because, as a result of the shorter measurement time, the temporal resolution is better than that of picture $PIC_{PRIOR}$. However the tomosynthesis picture still contains artifacts which arise as a result of incompleteness of the measurement data. These are referred to as "limited view angle" artifacts. They are particularly noticeable in that in those directions for which no projections are available for picture reconstruction, distortions are visible within the picture.

The parts T1 and T2 should be symmetrically placed in respect of the point in time of the optimum heart phase, which corresponds to the picture $PIC_{PRIOR}$. This means that the incomplete measurement data area included for the tomosynthesis picture lies centrally in the middle of the complete measurement data area of the picture $PIC_{PRIOR}$. Since as result of the Fourier slice theorem the frequency spectrum of the picture and of the measurement dataset are correlated, the information relating on the one hand to the central location of parts T1 and T2 in relation to the optimum heart phase and on the other hand to the central location of the incomplete measurement data area in relation to the complete measurement data area is equivalent.

As a result of the improved time resolution the masked picture is at least under some circumstances used as the basis for the picture $PIC_{FINAL}$ to be output as the result. Since however this, because of the distance of the sphere depicted in FIG. 5B would to a great extent feature the "limited view angle" artifacts, the component T3 shown bright is not removed from the picture data.

One would arrive at the component T3 shown bright by subjecting the picture $PIC_{PRIOR}$ to lowpass filtering with an edge filter. This edge filter thus cuts out the circle T3 from the picture data and suppresses the pixels outside the circle T3. Accordingly on the left-hand side of FIG. 6 it is specified that this part T3 of the picture data corresponds to a low-pass-filtered version $PIC_{PRIOR}$ LoPass of the picture $PIC_{PRIOR}$. The contrast information of the original picture is contained in the picture $PIC_{PRIOR}$ LoPass containing the low frequencies. By contrast the edge information of the original picture is contained in a picture containing the high frequencies; accordingly a reduction of the local sharpness has been brought about by the lack of some high frequencies because of the masking.

Thus not only the picture data of the tomosynthesis picture is used by the masking and thereby the complete cone of FIG. 5B discarded, but the spherical gaps of FIG. 5B are filled out for small frequencies with the lowpass-filtered picture data of the picture $PIC_{PRIOR}$. In those frequency areas in which parts T1 and T3 or T2 and T3 intersect, either the picture data of the tomosynthesis picture or that of the lowpass-filtered version $PIC_{PRIOR}$ LoPass of the picture $PIC_{PRIOR}$ will be used; because of the edge filter the lowpass-filtered picture data $PIC_{PRIOR}$ LoPass is not changed in relation to the picture data of the tomosynthesis picture.

After the masking MASK in which the picture data of the white parts T4 and T5 have been removed in the frequency space, a two-dimensional inverse Fourier transformation INV FOURIER is carried out, i.e. a back transformation of the picture data from the frequency area into the location area. The resulting picture $PIC_{MBF}$ has an improved temporal resolution in relation to the original picture $PIC_{PRIOR}$. I.e. the movement artifacts of the picture $PIC_{PRIOR}$ have been reduced by the masking. The disadvantage however is that the removal of picture data causes limited angle artifacts which were not present in the picture $_{PIC}$PRIOR.

The picture $PIC_{MBF}$ is improved in relation to the tomosynthesis picture since the limited angle artifacts of an unmodified tomosynthesis picture are reduced. This is based on the fact that the frequency content of the tomosynthesis picture has been supplemented in the low frequencies. This is based on the knowledge that the movement artifacts of the picture $PIC_{PRIOR}$ are mainly evident in the high-frequency components of picture $PIC_{PRIOR}$. Thus no damage is caused in respect of movement artifacts if the low-frequency picture component of the tomosynthesis picture is improved in respect of the gaps in the presence of picture data in the frequency space. Conversely a good temporal resolution of the tomosynthesis picture is little influenced by the modification in the low-frequency area, since the temporal resolution is contained in the higher frequencies.

Figure 7A:
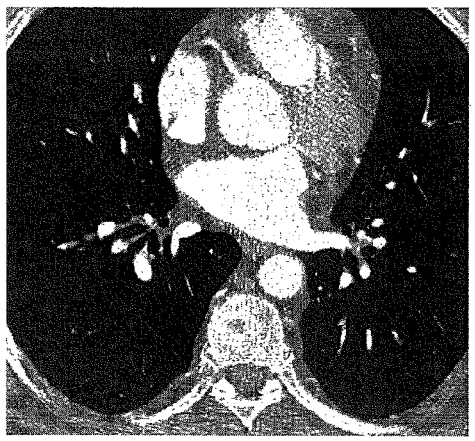
FIG. 7: two CT pictures.
Figure 7B:
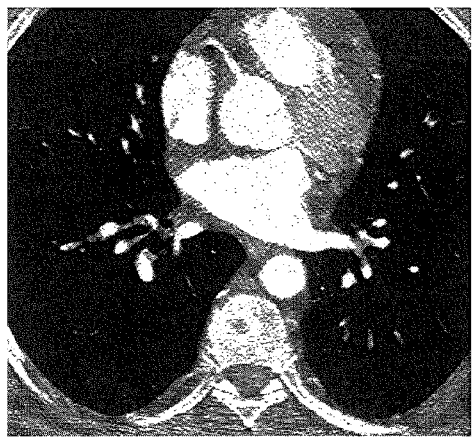

The frequency range of the picture $PIC_{MBF}$ in accordance with the masking according to FIG. 6 causes an anisotropic point spread function to be present whereby the noise texture of the picture $PIC_{MBF}$ is anisotropic. This can be illustrated on the basis of the CT pictures of FIG. 7. FIG. 7A shows a picture $PIC_{PRIOR}$ with a full frequency spectrum, and FIG. 7B a frequency-manipulated picture $PIC_{NBF}$ with directed noise.

Because of this worsened noise texture, which corresponds to a directed sharpness, it is only sensible to use the picture $PIC_{NBF}$ if this actually serves to avoid movement artifacts. It is therefore proposed to combine the pictures $PIC_{PRIOR}$ and $PIC_{NBF}$ in step MIX in order to obtain the result picture $PIC_{FINAL}$. This combination is carried out pixel-by-pixel depending on the local presence of movement.

To this end a further CT picture $PIC(t_2)$ is first computed from the measurement data. As with picture $PIC_{PRIOR}$, this computation is done for each slice of the area of the object under examination to be mapped so that a complete picture stack is present. The picture $PIC(t_2)$ differs from the picture $PIC_{PRIOR}$ by the point in time that it depicts. Compared to the picture $PIC_{PRIOR}$ it is offset slightly in time, i.e. shows a slightly earlier or slightly later time in the movement phase of the object under examination. A differential picture between the picture $PIC_{PRIOR}$ and the picture $PIC(t_2)$ is now computed for each slice. The values of this differential picture only lie in the area of moving structures above the picture noise. On the basis of the differential picture it can thus be determined in which picture regions movement artifacts occur in the picture $PIC_{PRIOR}$.

The result picture $PIC_{FINAL}$ is produced as a linear combination of:

$$PIC_{FINAL} = (1-\lambda) \cdot PIC_{MBF} + \lambda \cdot PIC_{Prior} \qquad \text{Formula (1)}$$

with the coefficient matrix $\lambda$ $$\lambda = \exp\left(-\frac{|PIC(t_2) - PIC_{Prior}|^2}{(\kappa \cdot \sigma)^2}\right) \qquad \text{Formula (2)}$$

In this case $\sigma^2$ is the locally-defined variance in picture $PIC_{PRIOR}$ and $\kappa$ is a scaling factor which can also be 1. The variance specifies how great the noise is at each pixel of the picture $PIC_{PRIOR}$. It can be determined for example by computing pixel-by-pixel the variances in the different spatial directions in a specific environment around the pixel considered in each case; subsequently an average is formed, with a boxcar function for example.

Instead of the exponential function in formula (2), there can be another type of dependency which, like the exponential function, causes the following:

The combination specified in formula (1) means that the frequency filter, i.e. the picture $PIC_{NBF}$, is only or mainly effective in moving picture areas. Then in a picture region with much movement the difference $PIC(t_2)-PIC_{Prior}$ is large, so that the coefficient matrix $\lambda$ is small here. In the complementary area, i.e. in the non-moving picture regions or those with little movement, the picture $PIC_{PRIOR}$ is mainly used, so that here its picture texture is retained as far as possible. This is because in a picture region with little movement the difference $PIC(t_2)-PIC_{Prior}$ is small, so that the coefficient matrix $\lambda$ here is approximately equal to 1.

The relating of the difference $PIC(t_2)-PIC_{Prior}$ to the noise means that the absolute size of the difference is not taken into consideration but rather the contrast-to-noise ratio of the movement. I.e. the coefficient matrix $\lambda$ indicates much movement, in accordance with $\lambda \approx 0$ if the difference is large in relation to the noise and little movement, in accordance with $\lambda \approx 1$ if the difference is smaller than the noise.

$PIC_{FINAL}$ is thus obtained as a result picture, a picture which the temporal resolution is increased compared to picture $PIC_{PRIOR}$. Because of the type of masking the limited angle artifacts themselves are largely avoided in moving picture areas. In addition the picture texture of the result picture $PIC_{FINAL}$ is similar to that of the picture $PIC_{PRIOR}$, since only in moving picture regions is reference made back to picture $PIC_{MBF}$ with the worsened picture texture.

Previously it has been assumed that in the masking in accordance with FIG. 6 the cutout frequency area lies centrally in relation to the optimum heart phase of the picture $PIC_{PRIOR}$. This assumption will be departed from below.

The movement functions of the coronary arteries are generally very complex. I.e. depending on the location within the heart, the different components of the heart move at different points in time in different directions. It is evident from this that, at a specific point in time for a specific region of the heart, information from specific directions is more or less important for the reconstruction of a CT picture. If the projections are cut out orthogonally to the direction of movement, the movement information is missing in this direction.

Through the type of masking information of the measurement data is cut out from a specific projection angle range. Were one to change the masking, information would be removed from another projection angle range. It can thus be established that, depending on the time of the picture $PIC_{PRIOR}$ and depending on the location within the object under examination, a different masking would lead to improved or worsened results in respect of the movement artifacts.

Furthermore the type of masking, as described above, causes an undesired anisotropy of the noise or of the picture sharpness. This anisotropy also depends both in respect of its extent and also in respect of its direction on the position of the cut out areas T4 and T5 in accordance with FIG. 6.

For these two effects, i.e. for the occurrence of the movement artifacts and the picture texture of the tomosynthesis picture it is true that depending on the mask used the one the effect of the other effect predominates. In addition the two effects can also interact so that they can reduce or worsen each other. This behavior is difficult to predict. It is thus proposed to carry out the method in accordance with FIG. 4 with different types of mask and to compare the result pictures $PIC_{FINAL}$.

Different masks are obtained by turning the areas T4 and T5 of FIG. 6 synchronously slightly in the same direction. In this way the position of the incomplete measurement dataset changes by comparison with the complete measurement dataset of the picture $PIC_{PRIOR}$. A specific number of turns is carried out with a selected, preferably constant, spacing. For example 32 different positions of the areas T4 and T5 can be used by turning, until the original mask of FIG. 6 is present again. In the measurement data space this corresponds to the cutting out of different projection angle areas in the 180° sinogram.

A picture $PIC_{NBF}$ and from this a result picture $PIC_{FINAL}$ are computed from the various masks. Thus a plurality of result pictures $PIC_{FINAL}$ is present which can be compared to each other in respect of picture quality. This comparison can be done visually, i.e. the best-looking of the result pictures $PIC_{FINAL}$ is selected. As an alternative to this a picture standard can be optimized. In this case the picture standard is applied to each of the results pictures $PIC_{FINAL}$ and the picture with the best picture standard is selected. For example the l1 Norm, i.e. the sum of the amount of the pixel values, can be used. In such cases one can start from the assumption that pictures with many artifacts have a higher value of the standard, so that the picture with the lowest l1 standard is selected as the result picture.

The invention has been described above using an example embodiment. It goes without saying that numerous changes and modifications are possible without departing from the framework of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing picture data of a moving object under examination from measurement data, the measurement data having been recorded during a relative rotational movement between a radiation source of a computed tomography system and the object under examination, the method comprising:
   computing first picture data from a complete measurement dataset of the measurement data for a computed tomography picture reconstruction;
   computing second picture data from an incomplete measurement dataset of the measurement data for a computed tomography picture reconstruction; and
   combining the first picture data and the second picture data into third picture data, the combining being computed using location-dependent movement information of the object under examination.

2. The method as claimed in claim 1, wherein the second picture data is computed by frequency components of the first picture data being removed.

3. The method as claimed in claim 2, wherein the frequency components are removed by application of a filter function.

4. The method as claimed in claim 3, wherein, during the removal, an area of relatively smaller frequencies exists for which no picture data is removed and an area of relatively larger frequencies exists for which picture data is removed.

5. The method as claimed in claim 3, wherein the filter function corresponds to cutting out two cone-shaped components and a partial refilling of the cone-shaped components.

6. The method as claimed in claim 5, wherein, during the removal, an area of relatively smaller frequencies exists for which no picture data is removed and an area of relatively larger frequencies exists for which picture data is removed.

7. The method as claimed in claim 2, wherein, during the removal, an area of relatively smaller frequencies exists for which no picture data is removed and an area of relatively larger frequencies exists for which picture data is removed.

8. The method as claimed in claim 1, wherein the second picture data is computed by components of the complete measurement dataset being removed.

9. The method as claimed in claim 1, wherein the incomplete measurement dataset is a subset of the complete measurement dataset.

10. The method as claimed in claim 1, wherein, the incomplete measurement dataset lies centrally within the complete measurement dataset.

11. The method as claimed in claim 1, wherein the combination is computed as a pixel-by-pixel weighted sum of the first and the second picture data.

12. The method as claimed in claim 11, wherein at least one weighting factor is used which contains the movement information.

13. The method as claimed in claim 12, wherein the weighting factor contains location-dependent noise information of the first picture data.

14. The method as claimed in claim 1, wherein, the second picture data, for the combination in moving picture regions, and the first picture data, in non-moving picture regions, contributes to the third picture data.

15. The method as claimed in claim 14, wherein the location-dependent movement information is obtained by fourth picture data being computed and compared pixel-by-pixel with the first picture data.

16. The method as claimed in claim 1, wherein the location-dependent movement information is obtained by fourth picture data being computed and compared pixel-by-pixel with the first picture data.

17. The method as claimed in claim 1, wherein a timespan of the object under examination with relatively small movement is determined and the complete measurement dataset was recorded during the timespan.

18. The method as claimed in claim 1, wherein a plurality of second picture data and, by combination with the first picture data, a plurality of third picture data is computed, and wherein result data is selected from the plurality of the third picture data.

19. The method as claimed in claim 18, wherein the plurality of second picture data differs from each other by the position of the respective incomplete measurement dataset within the complete measurement dataset.

20. The method as claimed in claim 19, wherein the selection is made by applying a picture standard to the plurality of the third picture data.

21. The method as claimed in claim 18, wherein the selection is made by applying a picture standard to the plurality of the third picture data.

22. A non-transitory computer-readable medium including a computer-program product, the computer program product comprising computer program segments, which when executed by a computer, causes the computer to perform the method as claimed in claim 1.

23. A control and processing unit for reconstruction of picture data of an object under examination from measurement data of a CT system, comprising:
   a program memory configured to store a program code, the program code being present in the program memory to, when executed, perform the following,
   computing first picture data from a complete measurement dataset of the measurement data for a computed tomography picture reconstruction;
   computing second picture data from an incomplete measurement dataset of the measurement data for a computed tomography picture reconstruction; and
   combining the first picture data and the second picture data into third picture data, the combining being computed using location-dependent movement information of the object under examination.

24. A CT system with a control and processing unit according to claim 23.

* * * * *